US006753324B2

(12) United States Patent
Jomaa

(10) Patent No.: US 6,753,324 B2
(45) Date of Patent: Jun. 22, 2004

(54) PHOSPHOROUS ORGANIC COMPOUNDS AND THEIR USE

(76) Inventor: Hassan Jomaa, Breslauer Strasse 24, Giessen (DE), D-35398

( * ) Notice: Subject to any disclaimer, the term of this patent is extended or adjusted under 35 U.S.C. 154(b) by 0 days.

(21) Appl. No.: 10/241,346

(22) Filed: Sep. 11, 2002

(65) Prior Publication Data

US 2003/0036533 A1 Feb. 20, 2003

Related U.S. Application Data

(62) Division of application No. 09/743,979, filed as application No. PCT/EP99/04827 on Jul. 9, 1999, now abandoned.

(30) Foreign Application Priority Data

Jul. 15, 1998 (DE) .......................................... 198 31 639
Sep. 22, 1998 (DE) .......................................... 198 43 360

(51) Int. Cl.$^7$ .............................................. A61K 31/66
(52) U.S. Cl. .......................... 514/114; 562/11; 562/808
(58) Field of Search .............................. 562/11, 8, 808, 562/809; 514/75, 114

(56) References Cited

U.S. PATENT DOCUMENTS

| 3,584,043 A | * | 6/1971 | Maier .......................... 562/808 |
| 4,038,311 A | * | 7/1977 | Kiefer et al. ................ 562/846 |
| 4,656,298 A | * | 4/1987 | Dingwall et al. ............. 556/12 |
| 4,693,742 A | | 9/1987 | Patterson |

FOREIGN PATENT DOCUMENTS

| DE | 27 33 658 | 2/1978 |
| EP | 0 009 686 | 4/1980 |
| JP | 61106504 | 5/1986 |

OTHER PUBLICATIONS

CA:112:56277 abs of DE3900085 Jul. 1989.*
Chemical Abstracts, vol. 111, No. 11, Sep. 11, 1989, Columbus, Ohio, US; abstract No. 092699, Khomutov A R "New Carnosine Synthetase Inhibitors Derived from.beta.–alanyl adenylate and .beta.–alanyl phosphate", XP002122511 Zusammenfassung & Bioorg. Khim. (BIKHD7, 01323423); 1989; vol. 15 (5); pp. 627–633, N.D. Zelinskii Inst. Org. Chem.; Moscow; USSR (SU).
Chemical Abstracts, vol. 093, No. 19, Nov. 10, 1980, Columbus, Ohio US; abstract No. 186456, Kamiya T et al,: "Studies on new phosphonic acid–containing antibiotics: synthesis of FR–315564 and related antibiotics" XP002122512 abstract & Curr. Chemother. Infect. Dis., Proc. Int. Congr. Chemother., 11$^{th}$ (43MKAT); 1980; vol. 1,; pp. 355–358, Fujisawa Pharm. Co., Ltd.,; Res. Lab.; Osaka; Japan.
Glabe A R et al.: "Novel Functionalized Acylphosphonates as Phophonoformate Analogs" Journal of Organic Chemistry, US, American Chemical Society, Easton, vol. 61, No. 20, p. 7212–7216 XP000627289 ISSN: 0022–3263.

H C Neu et al: "In Vitro and In Vivo Antibacterial Activity of FR–31564, a Phosphonic Acid Antimicrobial Agent" Antimicrobial Agents and Chemotherapy, US American Society for Microbiology, Washington , DC, vol. 19, No. 6, p. 1013–1023–1023 XP002113260 ISSN: 0066–4804.
H C Neu et al: "Synergy of Fosmidomycin (FR–31564) and Other Antimicrobial Agents" Antimicrobial Agents and Chemotherapy, US, American Society for Microbiology, Washington, DC, vol. 22, No. 4, p. 560–563–563 XP002113261 ISSN: 0066–4804.
D Greenwood: "Fosfomycin Trometamol: Activity In Vitro against Urinary Tract Pathogens" Infection, DE, MMV Medizin Verlag, Muenchen, Bd. 18, Nr. Suppl. 02, Seite S60–S64–S64 XP002113262 ISSN: 0300–8126.
Chemical Abstracts, vol. 105, No. 19, Nov. 10, 1986 Columbus, Ohio, US; abstract No. 166897, Yamaji T et al: "N–Substituted alkyl amine phosphates as herbicides" XP002122513 Zusammenfassung & JP 61 106504 A (Teijin Ltd.; Japan).
CA:124:56104 abs Phosphorus, Sulfur Silicon and Related Elem by Mahran et al. 1985, 101 (1–4) pp 17–27.
CA:117:69925 abs of Synthesis by Neidlein et al 50 pp 443–6.
BRN:802550 (Beilstein) abs of J Org Chem by Kosolapoff 26 pag 1895 1961.

* cited by examiner

Primary Examiner—Jean F. Vollano
(74) Attorney, Agent, or Firm—Harness, Dickey & Pierce, P.L.C.

(57) ABSTRACT

Use of phosphorous organic compounds of general formula (I)

$$\begin{array}{c} R_1 \quad\quad\quad O \\ \diagdown \quad\quad\quad \| \\ N-B-P-R_3 \\ \diagup \quad\quad\quad | \\ R_2 \quad\quad\quad R_4 \end{array} \quad (I)$$

wherein B represents either an ether group of the formula (II)

$$\begin{array}{c} Y \\ | \\ -A_1-O-A_2-C- \\ | \\ Z \end{array} \quad (II)$$

or a keto group of the formula (III)

$$\begin{array}{c} O \\ \| \\ -A_3-C-A_4- \end{array} \quad (III)$$

or is a 5 or 6 membered cyclic compound,
and their use for preparing pharmaceutical compositions for the therapeutic and prophylactic treatment of infections in humans and animals due to viruses, bacteria, fungi, and parasites as well as their use as a fungicide, bactericide and herbicide in plants.

9 Claims, No Drawings

PHOSPHOROUS ORGANIC COMPOUNDS AND THEIR USE

This application is a divisional application of U.S. Ser. No. 09/743,979, filed Mar. 2, 2001, now abandoned, which was a U.S. National Phase Application of PCT/EP99/04827, filed Jul. 9, 1999.

The invention relates to phosphorous organic compounds and their salts, esters, and amides as well as their use for preparing pharmaceutical compositions for therapeutic and prophylactic treatment of infections in humans and animals caused by viruses, bacteria, fungi, and parasites and the use thereof as a fungicide, bactericide, and herbicide in plants. According to the invention the phosphorous organic compounds comprise phosphinoyl derivatives, phosphinic acid derivatives and phosphonic acid derivatives.

There is a serious need for the provision of preparations to enhance the treatment of humans and animals and the protection of plants, which preparations not only possess a strong efficacy but in contrast to other pharmaceutical compositions and plant protective agents, contain reduced side effects and lower environmental impact and therefore represent a lower risk to health for humans.

The object of the present invention is therefore to provide a substance which can be universally used in infections by viruses, bacteria, fungi, and parasites in humans and animals and as a fungicide, bactericide, and herbicide in plants and fulfils the conditions given above.

This object is achieved in a completely surprising manner by the group of substances defined in claim 1. This group of substances demonstrates an anti-infectious effect against viruses, bacteria, fungi, unicellular and multicellular parasites as well as a fungicidal, bactericidal and herbicidal effect in plants.

The phosphorous organic compounds according to the invention correspond to general formula (I):

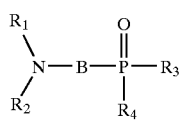

(I)

in which $R_1$ and $R_2$ are the same or different and are selected from the group, which consists of hydrogen, substituted and unsubstituted alkyl, substituted and unsubstituted hydroxyalkyl, substituted and unsubstituted alkenyl, substituted and unsubstituted alkinyl, substituted and unsubstituted aryl, substituted and unsubstituted acyl, substituted and unsubstituted cycloalkyl, substituted and unsubstituted aralkyl, substituted and unsubstituted heterocyclic radicals, halogen, $OX_1$ and $OX_2$, wherein $X_1$ and $X_2$ may be the same or different and are selected from the group, which consists of hydrogen, substituted and unsubstituted alkyl, substituted and unsubstituted hydroxyalkyl, substituted and unsubstituted alkenyl, substituted and unsubstituted alkinyl, substituted and unsubstituted aryl, substituted and unsubstituted acyl, substituted and unsubstituted cycloalkyl, substituted and unsubstituted aralkyl, substituted and unsubstituted heterocyclic radicals, B is selected from the group, which consists of ether group (II)

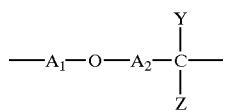

(II)

wherein $A_1$ and $A_2$, out of which $A_2$ also may be absent, are the same or different and are selected from the group, which consists of alkylene radicals, alkenylene radicals and hydroxyalkylene radicals, and Y and Z are hydrogen keto group (III)

(III)

wherein $A_3$ and $A_4$, out of which one or both may be absent, are the same or different, are selected from the group, which consists of alkylene radicals, alkenylene radicals and hydroxyalkylene radicals, and 5 and 6 membered cyclic, in particular heterocyclic compounds, which contain additionally to carbon at least one heteroatom as a ring member, wherein the heteroatom is selected from the group, which consists of oxygen and nitrogen, wherein $R_3$ and $R_4$ are the same or different and are selected from the group, which consists of hydrogen, substituted and unsubstituted alkyl having up to 26 carbon atoms, substituted and unsubstituted hydroxyalkyl having up to 26 carbon atoms, substituted and unsubstituted aryl, substituted and unsubstituted acyl, substituted and unsubstituted aralkyl, substituted and unsubstituted alkenyl having up to 26 carbon atoms, substituted and unsubstitlited alkinyl having up to 26 carbon atoms, substituted and unsubstituted cycloalkyl, substituted and unsubstituted heterocyclic radicals, halogen, $OX_3$ or $OX_4$, wherein $X_3$ or $X_4$ may be the same or different and are selected from the group, which consists of hydrogen, substituted and unsubstituted alkyl having up to 26 carbon atoms, substituted and unsubstituted hydroxyalkyl having up to 26 carbon atoms, substituted and unsubstituted aryl, substituted and unsubstituted aralkyl, substituted and unsubstituted alkenyl having up to 26 carbon atoms, substituted and unsubstituted alkinyl having up to 26 carbon atoms, substituted and unsubstituted cycloalkyl, substituted and unsubstituted heterocyclic radicals, a silyl, a cation of an organic and inorganic base, in particular a metal of the first, second, or third main group of the periodic system, ammonium, substituted ammonium and ammonium compounds which derive from ethylene diamine or amino acids, and their pharmaceutically acceptable salts, esters and amides and salts of the esters.

Compounds which correspond to formula (IV) are particularly preferred

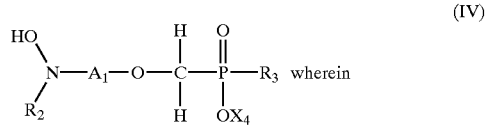

(IV)

$R_2$ is selected from the group, which consists of acetyl and formyl, $A_1$ is selected from the group, which consists of methylene, ethylene, ethenylene, hydroxyethylene, 2-hydroxypropylene, and $R_3$ is selected from the group, which consists of hydrogen, methyl, ethyl, hexadecyl, octadecyl and $OX_3$, and $X_3$ and $X_4$ are selected from the group, which consists of hydrogen, sodium, potassium, methyl, ethyl, hexadecyl, and octadecyl and, as far as both are present, may be the same or different.

Preferably the chain —A$_1$—O—C(ZY)— consists of one oxygen atom and two or three carbon atoms (substituents not included), particularly preferably two carbon atoms.

Out of the ether compounds those compounds are particularly preferred which are selected from the group, which consists of ((N-formyl-N-hydroxyamino)-methoxy)-methylphosphonic acid disodium salt, ((N-acetyl-N-hydroxyamino)-methoxy)-methyl phosphonic acid disodium salt, (2-(N-formyl-N-hydroxyamino)-etheneoxy) methylphosphonic acid disodium salt, (2-(N-acetyl-N-hydroxyamino)etheneoxy)-methyl-phosphonic acid disodium salt, (3-(N-formyl-N-hydroxyamino)-2-hydroxypropoxy)-methylphosphonic acid disodium salt, (3-(N-acetyl-N-hydroxyamino)-2-hydroxypropoxy)-methylphosphonic acid disodium salt.

Furthermore compounds are preferred, which correspond to formula (V)

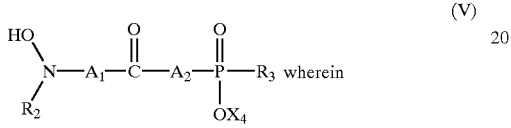

(V)

wherein

R$_2$ is selected from the group, which consists of acetyl and formyl,

A$_1$ is selected from the group, which consists of methylene, ethylene, ethenylene, hydroxymethylen, hydroxyethylene and 2-hydroxypropylene, A$_2$ is absent or methylene, R$_3$ is selected from the group, which consists of hydrogen, methyl, ethyl, hexadecyl, octadecyl and OX$_3$, and X$_3$ and X$_4$ are selected from the group, which consists of hydrogen, sodium, potassium, methyl, ethyl, hexadecyl and octadecyl and, as far as both are present, may be the same or different.

Preferably the chain —A$_1$—CO—A$_2$— consists of two to four carbon atoms (substituents not included), particularly preferably of three carbon atoms.

Out of these compounds 2-(N-formyl-N-hydroxyamino)-1-oxoethylphosphonic acid disodium salt, 2-(N-acetyl-N-hydroxyamino)-1-oxoethylphosphonic acid disodium salt, 3-(N-formyl-N-hydroxyamino)-1-oxopropylphosphonic acid disodium salt, 3-(N-acetyl-N-hydroxyamino)-1-oxopropylphosphonic acid disodium salt, 3-(N-formyl-N-hydroxyamino)-1-oxo-2-propenylphosphonic acid disodium salt, 3-(N-acetyl-N-hydroxyamino)-1-oxo-2-propenylphosphonic acid disodium salt, 4-(N-formyl-N-hydroxyamino)-1-oxo-3-hydroxybutylphosphonic acid disodium salt, 4-(N-acetyl-N-hydroxyamino)-1-oxo-3-hydroxybutylphosphonic acid disodium salt, 3-(N-formyl-N-hydroxyamino)-2-oxopropylphosphonic acid disodium salt, 3-(N-acetyl-N--hydroxyamino)-2-oxoproylphosphonic acid disodium salt, 4-(N-formyl-N-hydroxyamino)-3-oxo-2-hydroxy-2-methylbutylphosphonic acid disodium salt, 4-(N-acetyl-N-hydroxyamino)-3-oxo-2-hydroxy-2-methylpropylphosphonic acid disodium salt, 4-(N-formyl-N-hydroxyamino)-3-oxo-2-hydroxy-2-(hydroxymethyl)-butyl-phosphonic acid disodium salt, 4-(N-acetyl-N-hydroxyamino)-3-oxo-2-hydroxy-2-(hydroxymethyl)-propylphosphonic acid disodium salt prove to be particularly preferred.

In the cyclic compounds the amino group and the phosphorus atom may be bound to optional C atoms of the ring. However, compounds are preferred, in which they are bound to two C atoms which are separated only by one further atom. In the heterocyclic compounds the two carbon atoms are preferably separated by one heteroatom.

The following compounds are particularly preferred:

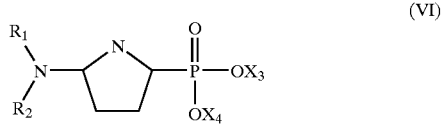

(VI)

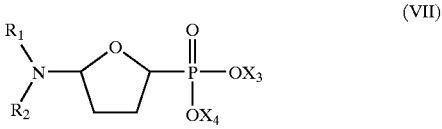

(VII)

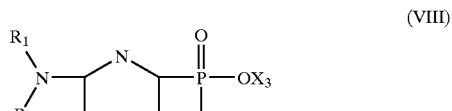

(VIII)

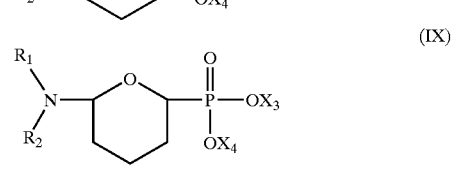

(IX)

Special features of the above definitions and suitable examples thereof are given below.

"Acyl" is a substituent which originates from an acid such as from an organic carboxylic acid, carbonic acid, carbamic acid or the thioacid or imidic acid corresponding to the individually present acids, or from an organic sulfonic acid, wherein in each case these acids comprise aliphatic, aromatic and/or heterocyclic groups in the molecule as well as carbamoyl or carbamimidoyl.

Suitable examples of these acyl groups were given below:

Acyl radicals originating from aliphatic acid are designated as aliphatic acyl groups and include:

Alkanoyl (e.g. formyl, acetyl, propionyl, butyryl, isobutyryl, valeryl, isovaleryl, pivaloyl etc.);

alkenoyl (e.g. acryloyl, methacryloyl, crotonoyl etc.);

alkylthioalkanoyl (e.g. methylthioacetyl, ethylthioacetyl etc.)

alkane sulfonyl (e.g. mesyl, ethane sulfonyl, propane sulfonyl etc.);

alkoxycarbonyl (e.g. methoxycarbonyl, ethoxycarbonyl, propoxycarbonyl, isopropoxycarbonyl, butoxycarbonyl, isobutoxycarbonyl etc.);

alkylcarbamoyl (for example methylcarbamoyl etc.);

(N-alkyl)-thiocarbamoyl (e.g. (N-methyl)-thiocarbamoyl etc.);

alkylcarbamimidoyl (e.g. methylcarbamimidoyl etc.);

oxalo;

alkoxalyl (e.g. methoxalyl, ethoxalyl, propoxalyl etc.).

In the above examples of aliphatic acyl groups the aliphatic hydrocarbon part, in particular the alkyl group and the alkane radical may optionally contain one or more suitable substituents, such as amino, halogen (e.g. fluorine, chlorine, bromine etc.), hydroxy, hydroxyimino, carboxy, alkoxy (e.g. methoxy, ethoxy, propoxy etc.), alkoxycarbonyl, acylamino (e.g. benzyloxycarbonylamino etc.), acyloxy (e.g. acetoxy, benzoyloxy etc.) and the like. Preferred aliphatic acyl radicals with such substituents are for example alkanoyls substituted with amino, carboxy, amino, and carboxy, halogen, acylamino or the like.

Acyl radicals originating from an acid with substituted or unsubstituted aryl groups, wherein the aryl group may comprise phenyl, toluyl, xylyl, naphthyl and the like are designated as aromatic acyl radicals. Suitable examples are given below:

Aroyl (e.g. benzoyl, toluoyl, xyloyl, naphthoyl, phthaloyl etc.);
Aralkanoyl (for example phenylacetyl etc.);
Aralkenoyl (for example cinnamoyl etc.);
Aryloxyalkanoyl (for example phenoxyacetyl etc.);
Arylthioalkanoyl (for example phenylthioacetyl etc.);
Arylaminoalkanoyl (for example N-phenylglycyl, etc.);
Arene sulfonyl (for example benzene sulfonyl, tosyl bzw. toluene sulfonyl, naphthalene sulfonyl etc.);
Aryloxycarbonyl (for example phenoxycarbonyl, naphthyloxycarbonyl etc.);
Aralkoxycarbonyl (for example benzyloxycarbonyl etc.);
Arylcarbamoyl (e.g. phenylcarbamoyl, naphthylcarbamoyl etc.);
Arylglyoxyloyl (for example phenylglyoxyloyl etc.).

In the present examples of aromatic acyl radicals the aromatic hydrocarbon part (in particular the aryl radical) and/or the aliphatic hydrocarbon part (in particular the alkane radical) may optionally contain one or more suitable substituents, such as those which were already mentioned as suitable substituents of the alkyl group and the alkane radical. In particular and as an example for preferred aromatic acyl radicals with particular substituents, aroyl substituted with halogen and hydroxy or with halogen and acyloxy and acyloxy and aralkanoyl substituted with hydroxy, hydroxyimino, dihalogenalkanoyloxyimino are mentioned as well as arylthiocarbamoyl (for example phenylthiocarbamoyl etc.);
arylcarbamimidoyl (for example phenylcarbamimidoyl etc.).

A heterocyclic acyl radical is understood to be an acyl radical which originates from an acid with heterocyclic group. These include:

Heterocyclic carbonyl in which the heterocyclic radical is an aromatic or aliphatic 5 to 6 membered heterocycle and has at least one heteroatom from the group nitrogen, oxygen and sulfur (for example thiophenyl, furoyl, pyrrolcarbonyl, nicotinoyl etc.);

heterocyclic alkanoyl, in which the heterocyclic radical is 5 to 6 membered and has at least one heteroatom from the group nitrogen, oxygen and sulfur (for example thiophenyl-acetyl, furylacetyl, imidazolylpropionyl, tetrazolylacetyl, 2-(2-amino-4-thiazolyl)-2-methoxyiminoacetyl etc.) and the like.

In the above examples of heterocyclic acyl radicals the heterocycles and/or the aliphatic hydrocarbon part may optionally contain one or more suitable substituents, such as the same as those which were mentioned as suitable for alkyl and alkane groups.

"Alkyl" is a straight- or branched-chain alkyl radical having up to 9 carbon atoms, unless defined otherwise, such as methyl, ethyl, propyl, isopropyl, butyl, isobutyl, tert.-butyl, pentyl, hexyl and the like.

"Hydroxyalkyl" is a straight- or branched-chain alkyl radical having up to 9 carbon atoms, unless defined otherwise, which at least comprises one hydroxy group, preferably one or two hydroxy groups.

"Alkenyl" includes straight- or branched-chain alkenyl groups with up to 9 carbon atoms, unless defined otherwise, for example vinyl, propenyl (for example 1-propenyl, 2-propenyl), 1-methylpropenyl, 2-methylpropenyl, butenyl, 2-ethylpropenyl, pentenyl, hexenyl.

"Alkinyl" includes straight- or branched-chain alkinyl radicals having up to 9 carbon atoms, unless defined otherwise.

Cycloalkyl preferably represents an optionally substituted $C_3$–$C_7$-cycloalkyl; possible substituents are e.g. alkyl, alkenyl, alkinyl, alkoxy (for example methoxy, ethoxy etc.), halogen (z.B. fluorine, chlorine, bromine etc.), nitro and the like.

Aryl is an aromatic hydrocarbon radical such as phenyl, naphthyl etc., which may optionally contain one or more suitable substituents such as alkoxy (for example methoxy, ethoxy etc.), halogen (for example fluorine, chlorine, bromine etc.), nitro and the like.

"Aralkyl" includes mono-, di-, triphenylalkyls such as benzyl, phenethyl, benzhydryl, trityl and the like, wherein the aromatic part may optionally contain one or more suitable substituents such as alkoxy (for example methoxy, ethoxy etc.), halogen (for example fluorine, chlorine, bromine etc.), nitro and the like.

"Alkylene" includes straight- or branched-chain alkylene groups, which contain up to 9 carbon atoms and may be represented by the formula

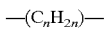
$$—(C_nH_{2n})—$$

in which n is an integer from 1 to 9, such as methylene, ethylene, trimethylene, methylethylene, tetramethylene, 1-methyltrimethylene, 2-ethylethylene, pentamethylene, 2-methyltetramethylene, isopropylethylene, hexamethylene, and the like. Preferred alkylene radicals contain up to 4 carbon atoms and radicals with 3 carbon atoms, such as for example trimethylene, are particularly preferred.

"Alkenylene" includes straight- or branched-chain alkenylene groups with up to 9 carbon atoms which may be reproduced by the formula:

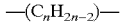
$$—(C_nH_{2n-2})—$$

in which n is an integer from 2 to 9, for example vinylene, propenylene (for example 1-propenylene, 2-propenylene), 1-methylpropenylene, 2-methylpropenylene, butenylene, 2-ethylpropenylene, pentenylene, hexenylene and the like. The alkenylene radical may particularly preferably contain up to 5 carbon atoms and in particular 3 carbon atoms, for example 1-propenylene. The hydrogen atoms may also be replaced by substituents, such as for example halogen radicals.

"Hydroxyalkylene" may include straight- or branched-chain alkylene radicals which contain up to 9 carbon atoms, wherein one or more selected carbon atoms are substituted with a hydroxy group. These radicals may be represented by the formula:

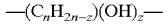
$$—(C_nH_{2n-z})(OH)_z—$$

in which n is an integer from 1 to 9 and z is an integer, to which $z \leq n$ applies. Suitable examples of such hydroxyalkylene groups include hydroxymethylene, hydroxyethylene (for example 1-hydroxyethylene and 2-hydroxyethylene), hydroxytrimethylene (for example 1-hydroxytrimethylene, 2-hydroxytrimethylene and 3-hydroxytrimethylene), hydroxytetramethylene (for example 2-hydroxytetramethylene), 2-hydroxy-2-methyltrimethylene, hydroxypentamethylene (for example 2-hydroxypentamethylene), hydroxyhexamethylene (for example 2-hydroxyhexamethylene) and the like. A lower hydroxyalkylene with up to 4 carbon atoms is particularly preferred and in particular one with 3 carbon atoms for example 2-hydroxytrimethylen. The hydrogen atoms may also be replaced by substituents, such as for example halogen radicals.

The 5 and 6 membered cyclic compounds, which may be represented by B, may be aromatic or aliphatic and substituted, for example by alkyl groups having up to 7 carbon atoms and hydroxy groups.

The 5 and 6 membered heterocyclic compounds, which may be represented by B and contain additionally to carbon at least one heteroatom as a ring member, may be saturated or unsaturated. Examples are azixane, diazixane, azixine, diazixine, azolane, diazolane, azol, diazol, oxolane, dioxolene, oxol, dioxol, oxixane, dioxixane, oxixine and dioxixine. They may be aliphatic or aromatic and may be substituted for example by alkyl groups having up to 7 carbon atoms and hydroxy groups.

Preferably, the radicals $X_3$ and $X_4$ may be selected such, that esters form on the phosphono group or the phosphino group. Suitable examples of esters of the compounds according to the formulae (I), (IV) to (IX) are suitable mono and diesters, and preferred examples of such esters include alkylester (for example methylester, ethylester, propylester, isopropylester, butylester, isobutylester, hexylester etc.); aralkyl ester (benzyl ester, phenethyl ester, benzohydryl ester, trityl ester etc.); aryl ester (for example phenyl ester, toluyl ester, naphthyl ester etc.); aroylalkyl ester (for example phenacyl ester etc.); and silylester (for example of trialkylhalogensilyl, dialkyldihalogensilyl, alkyltrihalogensilyl, dialkylarylhalogensilyl, trialkoxyhalogensilyl, dialkylaralkylhalogensilyl, dialkoxydihalogensilyl, trialkoxyhalogensilyl etc.) and the like.

With the above ester the alkane and/or arene part may optionally contain at least one suitable substituent such as halogen, alkoxy, hydroxy, nitro or the like.

$X_3$ and $X_4$ are preferably a metal of the first, second, or third main group of the periodic system, ammonium, substituted ammonium, or ammonium compounds, which derive from ethylene diamine or amino acids. In other words the salt compounds of the phosphorous organic compounds with organic or inorganic bases (for example sodium salt, potassium salt, calcium salt, aluminum salt, ammonium salt, magnesium salt, triethylamine salt, ethanolamine salt, dicyclohexylamine salt, ethylenediamine salt, N,N'-dibenzylethylene diamine salt etc.) as well as salts with amino acids (for example arginine salt, aspartic acid salt, glutamic acid salt etc.) and the like are formed.

The compounds according to the invention in accordance with the formulae (I) to (IX) may be present on their protonized form as an ammonium salt of organic or inorganic acids, such as hydrochloric acid, hydrobromic acid, sulfur acid, nitric acid, methanesulfonic acid, p-toluene sulfonic acid, acetic acid, lactic acid, maleic acid, fumaric acid, oxalic acid, tartaric acid, benzoic acid, etc.

The compounds according to the invention in accordance with the formulae (I), (IV) to (IX) permit for example the emergence of spatial isomers for groups containing double bonds or chiral groups $R_1$, $R_2$, $R_3$, $R_4$, $X_1$, $X_2$, $X_3$, $X_4$, $A_1$, $A_2$, $A_3$, $A_4$ and the heterocycles. The use of the compounds according to the invention includes all spatial isomers both as pure substances and in form of their mixtures.

The phosphorous organic compounds are in particular suited for the therapeutic and prophylactic treatment of infections in humans and animals caused by viruses, bacteria, unicellular and multicellular parasites and fungi.

The compounds are effective against unicellular parasites (protozoa), in particular against pathogens of malaria and the sleeping sickness as well as the Chagas' disease, the toxoplasmosis, amoebic dysentery, leishmaniasis, trichomoniasis, sarcocystosis, acanthamebiasis, naegleriasis, coccidiosis, giardiasis and lambliosis.

Therefore, they are particularly suitable as malaria prophylactics and as prophylactics of sleeping sickness as well as the Chagas' disease, toxoplasmosis, amoebic dysentery, leishmaniasis, trichomoniasis, pneumocystosis, balantidiasis, cryptosporidiasis, sarcocystosis, acanthamebiasis, naegleriasis, coccidiosis, giardiasis and lambliosis.

The active agents according to the invention may in particular be used against the following bacteria:

Bacteria of the family Propionibacteriaceae, in particular the genus Propionibacterium, in particular the species *Propionibacterium acnes*;

bacteria of the family Actinomycetaceae, in particular the genus Actinomyces;

bacteria of the genus Corynebacterium, in particular the species *Corynebacterium diphteriae* and *Corynebacterium pseudotuberculosis*;

bacteria of the family Mycobacteriaceae, the genus Mycobacterium, in particular the species *Mycobacterium leprae, Mycobacterium tuberculosis, Mycobacterium bovis* and *Mycobacterium avium*;

bacteria of the family Chlamydiaceae, in particular the species *Chlamydia trachomatis* and *Chlamydia psittaci*;

bacteria of the genus Listeria, in particular the species *Listeria monocytogenes*;

bacteria of the species *Erysipelthrix rhusiopathiae*;

bacteria of the genus Clostridium;

bacteria of the genus Yersinia, the species *Yersinia pestis, Yersinia pseudotuberculosis, Yersinia enterocolitica* and *Yersinia ruckeri*;

bacteria of the family Mycoplasmataceae, the genus Mycoplasma and Ureaplasma, in particular the species *Mycoplasma pneumoniae*; bacteria of the genus Brucella;

bacteria of the genus Bordetella;

bacteria of the family Neiseriaceae, in particular the genuses Neisseria and Moraxella, in particular the species *Neisseria meningitides, Neisseria gonorrhoeae* and *Moraxella bovis*;

bacteria of the family Vibrionaceae, in particular the genuses Vibrio, Aeromonas, Plesiomonas and Photobacterium, in particular the species *Vibrio cholerae, Vibrio anguillarum* and *Aeromonas salmonicidas*; bacteria of the genus Campylobacter, in particular the species *Campylobacter jejuni, Campylobacter coli* and *Campylobacter fetus*; bacteria of the genus Helicobacter, in particular the species *Helicobacter pylori*;

bacteria of the families Spirochaetaceae and the Leptospiraceae, in particular the genus Treponema, Borrelia and Leptospira, in particular *Borrelia burgdorferi*;

bacteria of the genus Actinobacillus;

bacteria of the family Legionellaceae, the genus Legionella;

bacteria of the family Rickettsiaceae and family Bartonellaceae;

bacteria of the genus Nocardia and Rhodococcus; bacteria of the genus Dermatophilus;

bacteria of the family Pseudomonadaceae, in particular the genuses Pseudomonas and Xanthomonas;

bacteria of the family Enterobacteriaceae, in particular the genuses Escherichia, Klebsiella, Proteus, Providencia, Salmonella, Serratia and Shigella; bacteria of the family Pasteurellaceae, in particular the genus Haemophilus;

bacteria of the family Micrococcaceae, in particular the genus Micrococcus and Staphylococcus; bacteria of the family Streptococcaceae, in particular the genus Streptococcus and Enterococcus and bacteria of the family Bacillaceae, in particular the genus bacillus and clostridium.

Therefore the phosphorous organic compounds are suitable for treatment of diphtheria, acne vulgaris, listeriosis, erysipelas in animals, gas gangrene in humans and in animals, diseases in humans and animals caused by clostridium septicum, tuberculosis in humans and animals, leprosy, and further mycobacteriosis in humans and animals, paratuberculosis in animals, pestis, mesenterial lymphadenitis and pseudotuberkulosis in humans and animals, cholera, legionnaires disease, borrelioses in humans and animals, leptospiroses in humans and animals, syphilis, campylobacter enteritides in humans and animals, moraxella keratoconjunctivitis and serositis in animals, brucelloses in animals and in humans, anthrax in humans and animals, actinomycosis in humans and animals, streptotrichosis, psittakosis/ornithosis in animals, Q-fever, ehrlichiosis.

Further the use is advantageous in helicobacter eradication therapy of ulcera of the gastrointestinal tract.

Further combinations with an additional antibiotic may also be used for treatment of the above mentioned diseases. As combined preparations with other antiinfective agents in particular isoniazide, rifampicin, ethambutol, pyrazinamide, streptomycin, protionamide and dapsone are suitable for the treatment of tuberculosis The active agents according to the present invention may furthermore be used in particular in infections with following viruses:

Parvoviridae: parvo viruses, dependo viruses, Denso viruses;

Adenoviridae: adeno viruses, mastadeno viruses, aviadeno viruses; Papovaviridae: papova viruses, in particular papilloma viruses (so called wart viruses), Polyoma viruses, in particular JC virus, BK virus, and miopapova viruses; herpes viruses: all herpes viruses, in particular herpes simplex viruses, the varizella-zoster viruses, human cytomegalo virus, Epstein-Barr viruses, all human herpes viruses, human herpes virus 6, human herpes virus 7, human herpes virus 8; Poxyiridae: pox viruses, orthopox, parapox, molluscum contagiosum virus, avipox viruses, capripox viruses, leporipox viruses; all primary hepatotropic viruses, Hepatitis viruses: hepatitis A viruses, hepatitis B viruses, hepatitis C viruses, hepatitis D viruses, hepatitis E viruses, hepatitis F viruses, hepatitis G viruses;

Hepadna viruses: all hepatitis viruses, hepatitis B virus, hepatitis D viruses; Picornaviridae: picorna viruses, all entero viruses, all polio viruses, all coxsackie viruses, all echo viruses, all rhino viruses, hepatitis A virus, aphtho viruses; Calciviridae: hepatitis E viruses; Reoviridae: reo viruses, orbi viruses, rota viruses; Togaviridae: toga viruses, alpha viruses, rubi viruses, pesti viruses, rubella virus;

Flaviviridae: flavi viruses, ESME virus, hepatitis-C-Virus;

Orthomyxoviridae: all influenza viruses; Paramyxoviridae: paramyxo viruses, morbilli virus, pneumo virus, measles virus, mumps virus; Rhabdoviridae: rhabdo viruses, rabies virus, lyssa virus, viscula stomatitis virus; *Corona viridae:* corona viruses; Bunyaviridae: bunya viruses, nairo virus, phlebo virus, uuku virus, hanta virus; Arenaviridae: arena viruses, lymphocytic choriomeningitis-virus; Retroviridae: retro viruses, all HTL viruses, human T-cell leukaemia virus, oncorna viruses, spuma viruses, lenti viruses, all HI-viruses; Filoviridae: Marburg and Ebola virus; Slow-virus-infections, prions; Onco viruses, leukemia viruses.

The phosphororganic compounds according to the invention are therefore suitable for fighting the following viral infections:

Eradication of papilloma viruses to prevent tumors, in particular tumors in the sexual organs caused by papilloma viruses in humans, eradication of JC viruses and BK viruses, eradication of herpes viruses, eradication of human herpes viruses 8 for the treatment of Kaposi's sarcoma, eradication of cytomegalo viruses before transplants, eradication of Eppstein-Barr viruses before transplants and to prevent tumors associated with Eppstein-Barr viruses, eradication of hepatitis viruses for the treatment of chronic liver diseases and for the prevention of tumors of the liver and cirrhosis of the liver, eradication of coxsackie viruses patients with cardiomyopathy, eradication of coxsackie viruses in diabetes mellitus patients, eradication of immune system debilitating viruses in humans and animals, treatment of secondary infections in AIDS-patients, treatment of inflammations of viral origin of the respiratory tract (larynx papillomas, hyberplasias, rhinitis, pharyngitis, bronchitis, pneumonias), of the sensory organs (Keratoconjunctivitis), of the nervous system (poliomyelitis, meningoenzephalitis, encephalitis, subacute sklerosing panencephalitis SSPE, progressive multifocal leukoencephalopathie, lymphocytic choriomeningitis), of the gastrointestinal tract (stomatitis, gingivostomatitis, oesophagitis, gastritis, gastroenteritis, diarrhoea-causing diseases), the liver and the gall bladder system (hepatitis, cholangitis, hepatocellular carcinoma), of the lymphatic tissue (mononucleosis, lymphadenitis), of the haematopoetic system, of the sexual organs (mumpsorchitis), of the skin (warts, dermatitis, herpes labialis, heat rush, herpes zoster, shingles), of the mucous membranes (papillomas, conjunctiva papillomas, hyperplasias, dysplasias), of the heart/blood vessel system (arteriitis, myocarditis, endocarditis, pericarditis), the kidney/urinary tract systems, of the sexual organs (anogenital lesions, warts, genital warts, acute condylomas, displasias, papillomas, cervix dysplasias, condylomata acuminata, epidermodysplasia verruci formis), of the organs of motion (myositis, myalgien), treatment of foot and mouth diseases in cloven-hoofed animals, of Colorado tick fever, of Dengue-syndrome, of haemorrhagic fever, of early summer meningoencephalitis (FSME) and of yellow fever.

The described compounds, i.e. the phosphorous organic compounds according to formulae (I), (IV) to (IX) and esters and amides thereof formed on the phosphono group or the phosphino group as well as salts thereof show a strong cytotoxic efficacy against bacteria, fungi, viruses, unicellular and multicellular parasites. Therefore the compounds according to the invention are usable in the treatment of infectious diseases caused by viruses, bacteria, parasites, and fungi in humans and animals. The compounds also are suited for use in prophylactics of diseases due to viruses, bacteria, parasites, and fungi, in particular in prophylactics of malaria and in prophylactics of the sleeping sickness.

The phosphorous organic compounds according to the invention which generally include pharmaceutically acceptable salts, amides, esters, a salt of such an esters or else compounds which upon application provide the compounds use according to the invention metabolic products or decomposition products, also called "prodrugs" may all be prepared for administration like known anti-infectious agents in any suitable manner (mixed with non-toxic pharmaceutically acceptable carriers).

Pharmaceutically acceptable salts of the aminohydrophosphonic acid derivative include salts, which form the compounds of formulae (I), (IV) to (IX) in their protonised form as an ammonium salt of inorganic or organic acids, such as hydrochloric acid, sulfur acid, citric acid, maleic acid, fumaric acid, tartaric acid, p-toluene sulfonic acid.

Salts which are formed by suitable selection of $X_3$ and $X_4$ are especially suited, such as sodium salt, potassium salt, calcium salt, ammonium salt, ethanolamine salt, triethylamine salt, dicyclohexylamine salt and salts of amino acid such as arginine salt, aspartic acid salt, glutamic acid salt.

The activity of substances is determined in a test system. This system is based on the measuring of the inhibition of growth of bacteria,-parasites, viruses, fungi or plants in vitro. To this end, test procedures are used, some of which are known to the person skilled in the art.

To determine the anti-malaria activity, for example, the inhibition of the growth of malaria parasites in blood cultures is determined.

The determining of the anti-bacterial activity, for example is based on the measurement of the inhibition of the growth of bacteria on culture media and in liquid cultures.

The determining of the anti-viral activity is based on the inhibition of the formation of viral elements in cell cultures.

The determining of fungicidal activity is based on the inhibition of the growth of fungi on culture media and in liquid cultures.

Some of the microorganism which should be investigated can only be investigated in animal models. In this case we will use the corresponding model.

Substances which demonstrate an efficacy in the in vitro measuring system will be further investigated in in vivo models.

The anti-parasitic, antiviral or fungicide activity will be further evaluated in the appropriate animal model.

The screening of herbicidal activity is determined by algae systems and measurement of the isoprene emission of plants at standard conditions.

The pharmaceutically effective preparations may be prepared in the form of pharmaceutical preparations in dispensing units. This means that the preparations can be present in the form of individual parts, for example tablets, dragees, capsules, pills, suppositories and ampoules, the active ingredient content of which corresponds to a fraction or a multiple of a single dose. The dispensing units can, for example, contain 1, 2, or 4 single doses or ½, ⅓ or ¼ of a single dose. A single dose preferably contains the quantity of active ingredient which is administered during one application and which usually corresponds to a whole, a half or third of a quarter of a daily dose.

Non-toxic, inert pharmaceutically suitable carriers are understood to mean solid, semi-solid or liquid di-uents, fillers and formulation auxiliary agents of all kinds.

Tablets, dragees, capsules, pills, granules, suppositories, solutions, suspensions and emulsions, pastes, ointments, gels, creams, lotions, powders and sprays are mentioned as preferred pharmaceutical preparations. Tablets, dragees, capsules, pills and granules may contain in addition to the conventional excipients the active ingredient, such as (a) fillers and diluents, for example starches, lactose, cane sucar, glucose, mannitol and silicic acid, (b) binders, for example carboxymethylcellulosis, alginate, gelatine, polyvinylpyrrolidone, (c) moisture-retaining agents, for example glycerol, (d) dispersing agents, for example agar-agar, calcium carbonate and sodium carbonate, (e) solution retarders, for example paraffin and (f) resorption accelerators, for example quaternary ammonium compounds, (g) wetting agents, for example cetyl alcohol, glycerol monostearate, (h) adsorption agents, e.g. kaolin and betonite and (i) lubricants, for example talcum, calcium and magnesium stearate and solid polyethylene glycol or mixtures of the substances listed under (a) to (i).

The tablets, dragees, capsules, pills and granules may be provided with the conventional coatings and casings optionally comprising opaquing agents and may also be put together so that they release the active ingredient or active ingredients only or preferably in a specific part of the intestinal optionally with sustain release, wherein polymer substances and waxes for example may be used as embedding compounds.

The active ingredient or the active ingredients may optionally also be present in microencapsulated form with one or more of the above mentioned excipients.

In addition to the active ingredient or the active ingredients suppositories may also contain the conventional water soluble or water insoluble excipients, for example polyethylene glycols, fats, for example cacoa fat and higher esters (for example $C_{14}$-alcohol with $C_{16}$-fatty acid) or mixtures of these substances.

In addition to the active ingredients ointments, pastes, creams and gels may contain the conventional excipients, for example animal and vegetable fats, waxes, paraffins, starch, tragacanth, cellulose derivative, polyethylene glycols, silicones, bentonites, silicic acid, talcum and zinc oxide or mixtures of these substances.

In addition to the active ingredients powders and sprays may contain the conventional excipients, for example lactose, talcum, silicic acid, aluminium hydroxide, calcium silicate and polyamide powder or mixtures of these substances. Sprays may additionally contain the conventional blowing agents, for example chlorofluorohydrocarbons.

In addition to the active ingredients solutions and emulsions may contain the conventional excipients such as solvents, solubilisers and emulgators, for example water, ethyl alcohol, isopropyl alcohol, ethyl carbonate, ethyl acetate, benzyl alcohol, benzyl benzoate, propyleneglycol, 1,3-butyleneglycol, dimethylformamide, oils, in particular cotton seed oil, peanut oil, corn oil, olive oil, castor oil and sesame oil, glycerol, glycerol formal, tetrahydrofurfuryl alcohol, polyethyleneglycols and fatty acid esters of sorbitan or mixtures of these substances.

The solutions and emulsions may also be present in sterile and blood isotonic form for parenteral application.

In addition to the active ingredients suspensions may contain conventional excipients such as liquid diluents, for example water, ethyl alcohol, propylene glycol, suspending agents, for example ethoxylated isostearyl alcohols, polyoxyethylene sorbitol and sorbitan esters, microcrystalline cellulose, aluminium metahydroxide, bentonite, agar-agar and tragacanth or mixtures of these substances.

The above-mentioned formulations can also contain dyes, preservatives and odour and flavour improving additives, for example peppermint oil and eucalyptus oil and sweeteners, for example saccharine.

The active agents of formulae (I), (IV) to (IX) should be present in the above listed pharmaceutical preparations preferably in a concentration of approximately 0.1 to 99.5% by weight, preferably of approximately 0.5 to 95% by weight of the total mixture.

In addition to the compounds of formulae (I), (IV) to (IX) the pharmaceutical preparations may also contain further pharmaceutical agents.

The compounds may be used with hereto described substances with antimicrobial, antiviral, antifungal and antiparasitic properties. Compounds which have already found application in treatment or are still being used belong in particular to this group. Substances which are listed in the Red List or Simon/Stille, Antibiotika-Therapie in Klinik und Praxis, 9.Auflage 1998 Schattauer Verlag, or under http://www.customs.treas.gov/imp-exp/rulings/harmoniz/hrm129.html on the Internet are particularly suitable for this purpose. In particular derivatives with penicillins, benzyl penicillin (Penicillin G), phenoxy penicillins, isoxazolyl penicillins, amino penicillins, ampicillin, amoxicillin, bacampicillin, carboxy penicillin, ticarcillin, temocillin, acyalamino penicillins, azlocillin, mezlocillin, piperacillin, apalcillin, mecillinam, cephalosporins, cefazolin group, cefuroxime group, cefoxitin group, cefoxitin, cefotetan, cefinetazole, latamoxef, flomoxef, cefotaxime group, cefozidime, ceftazidime group, ceftazidime, cefpirom, cefepim, remaining cephalosporins, cefsulodine, cefoperazone, oralcephalosporins of the cefalexin group, loracarbef, cefprozil, new oralcephalosporins with expanded spectrum, cefixime, cefpodoxime proxetil, cefuroxime axetil, cefetamet, cefotiam hexetil, cefdinir, ceftibutene, other β-lactam antibiotics, carbapenem, imipenem/ cilastatin, meropenem, biapenem, aztreonam, β-lactamase inhibitors, calvulanic acid/amoxicillin, Clavulanic acid/ ticarcillin, sulbactam/ampicillin, tazobactam/piperacillin, tetracyclines, oxytetracycline, rolitetracyclines, doxycycline, minocycline, chloramphenicol, aminoglycosides, gentamicin, tobramycin, netilmicin, amikacin, spectinomycin, macrolides, erythromycin, clarithromycin, roxithromycin, azithromycin, dirithromycin, spiramycin, josamycin, lincosamides, clindamycin, fusidic acid, glycopeptide antibiotics, vancomycin, tecoplanin, pristinamycin derivatives, fosfomycin, antimicrobial folic acid antagonists, sulphonamides, co-trimoxazole, trimethoprim, other diaminopyrimidine sulfonamide combinations, nitrofurans, nitrofurantoin, nitrofurazone, Gyrase inhibitors (quinolones), norfloxacin, ciprofloxacin, ofloxacin, sparfloxacin, enoxacin, fleroxacin, pefloxacin, lomefloxacin, Bay Y3118, nitroimidazoles, antimycobacterial agents, isoniazid, rifampicin, rifabutin, ethambutol, pyrazinamide, streptomycin, capreomycin, prothionamide, terizidon, dapsone, clofazimine, topical antibiotics, bacitracin, tyrothricin, polymyxins, neomycin, kanamycin, paromomycin, mupirocin, antiviral agents, acyclovir, ganciclovir, azidothymidine, didanosin, zalcitabin, thiacytidine, stavudin, ribavirin, idoxuridine, trifluridine, foscarnet, amantadine, interferons, tibol derivatives, proteinase inhibitors, antifungal agents, polyenes, amphothericin B, nystatin, natamycin, azoles, azoles for septic treatment, miconazole, ketoconazole, itraconazole, fluconazole, UK-109.496, azoles for topical application, clotrimazole, econazole, isoconazole, oxiconazole, bifonazole, flucytosine, griseofulvin, ciclopiroxolamine, tolnaftate, naftifine, terbinafine, amorolfine, antraquinones, betulinic acid, semianthrachinones, xanthones, naphtoquinones, aryaminoalcohols, quinine, quinidines, mefloquine, halofantrine, chloroquine, amodiaquine, acridine, benzonaphthyridine, mepacrine, pyronaridine, dapsone, sulphonamides, sulfadoxine, sulfalenes, trimethoprim, proguanil, chlorproguanil, diaminopyrimidines, pyrimethamine, primaquine, aminoquinolines, WR 238,605, tetracycline, doxycycline, clindamycin, norfloxacin, ciprofloxacin, ofloxacin, artemisinin, dihydroartemisinin, 10b arte mether, arte ether, arte sunate, atovaquon, suramin, melarsoprol, nifurtimox, stibogluconate-sodium, pentamidine, amphotericine B, metronidazole, clioquinole, mebendazole, niclosamide, praziquantel, pyrantel, tiabendazole, diethylcarbamazine, ivermectin, bithionol, oxamniquine, metrifonate, piperazine, embonate can [be used].

Furthermore the phosphorous organic compounds may be present in the pharmaceutical preparations in combination with sulfonamide, sulfadoxin, artemisinin, atovaquon, chinin, chloroquine, hydroxychloroquin, mefloquin, halofantrin, pyrimethamine, armesin, tetracycline, doxycyclin, proguanil, metronidazol, praziquantil, niclosamide, mebendazol, pyrantel, tiabendazole, diethylcarbazin, piperazin, pyrivinum, metrifonate, oxamniquin, bithionol or suramin or several of these substances.

The above listed pharmaceutical preparations are produced in the conventional manner by known methods, for example by mixing the active ingredient or active ingredients with the excipient or excipients.

The above-mentioned preparations can be used in humans and animals either orally, rectally, parentally, (intravenously, intramuscularly, subcutaneously), intracisternally, intravaginally, intraperitoneally, topically (powder, ointment, drops) and for the treatment of infections in cavities, orifices. Suitable preparations are injection solutions, solutions and suspensions for oral treatment, gels, infusions, emulsions, ointments or drops. Ophthalmological and dermatogical formulations, silver and other salts, eardrops, eye ointments, powders or solutions can be used for topical treatment. With animals the absorption can occur via the food or drinking water in suitable formulations. Furthermore gels, powders, tablets, sustain release tablets, premixes, concentrates, granules, pellets, tablets, boli, capsules, aerosoles, sprays, inhalers can be used with humans and animals. The compounds according to the invention can furthermore be incorporated into other carrier materials such as, for example, plastic materials (plasticchains for topical treatment), collagen or bone cement.

In general it has proved advantageous both in human and veterinary medicine to administer the active ingredient or ingredients of formulae (I), (IV) to (IX) in total quantities of approximately 0.05 to approximately 600, preferably 0.5 to 200 mg/kg body weight per 24 hours, optionally in the form of several individual doses in order to achieve the desired results. An individual dose contains the active ingredient or ingredients preferably in quantities of approximately 1 to approximately 200, in particular 1 to 60 mg/kg body weight. It may, however, be necessary to deviate from the above-mentioned dosages and this is dependent on the nature and the body weight of the patient to be treated, the nature and the severity of the disease, the nature and the method and the application of the pharmaceutical compositions as well as the time scale or interval within the administration takes place.

Thus in some cases it may be sufficient to get by with less than the above mentioned quantity of active ingredient, whilst in other cases the above-stated quantity of active ingredient must be exceeded. The person skilled in the art may determine the optimum dosage and method of application of the active ingredient in each case by virtue of his expert experience.

The compounds according to the invention may be administered in animals in the conventional concentrations and preparations together with the feed or feed preparations or the drinking water.

Furthermore compounds according, to the invention may be excellently used as bactericides, fungicides and herbicides in plants.

Principally a person skilled in the art knows which way of synthesis for preparing the substances according to the invention he has to choose. In the following some ways of synthesis for compounds of the invention are given by example.

Possible Ways of Synthesis of Compounds Looking Like

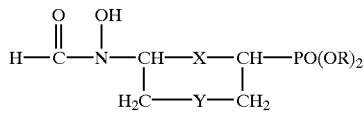

with R =  H or Na⁺ and X = —CH₂— Y = without Y (5 membered ring)  Example 1

= —CH₂— (6 membered ring)  Example 2

—O— = without Y (5 membered ring)  Example 3

= —CH₂— (6 membered ring)  Example 4

—NH— = without Y (5 membered ring)  Example 5

= —CH₂— (6 membered ring)  Example 6

EXAMPLE 1

3-Oxo-cyclopentylphosphonic acid diethylester 1(a)

0.52 mmol trimethylsilyltriflate are added dropwise to 11.4 mmol diethylphosphite and 12.4 mmol N,O-bis-(trimethylsilyl)acetamid in 5 ml dichlormethane at 0° C. After 30 minutes of stirring 0.52 mmol 2-cyclopenten-1-one are added dropwise thereto at the same temperature and stirring is continued for 1 h. The enolsilane intermediate product is hydrolized by 3 ml 1 n HCl and 3 hours of stirring. The organic phase is separated, dried over magnesiumsulfate and concentrated. The raw product may be chromatographed on $SiO_2$ and, after concentrating the desired fractions, results to 3-(phosphonic acid diethylester)-cyclopentan-1-one (a) with boiling point$_{0.25\ Torr}$=104° C. in a good yield.

(Compare I. Mori, Y. Kimura, T. Nakano, S. Matsunaga, G. Iwasaki, A. Ogawa, K. Hayakawa, Tetrahedron Letters 1997, 38, 3543–46, R. G. Harvey, Tetranedron 1966, 22, 2561–73 and E. Öhler, E. Zbiral, Liebigs Ann. Chem. 1991, 229–36)

3-(Phosphonic acid diethylester)-cyclopentanone oxime 1(b)

1.41 mmol N,O-bis-(trimethylsilyl)-hydroxyamine—dissolved in THF—are added to a suspension of 150 mg 35% potassiumhydrid in mineral oil—also dissolved in THF—and cooled to −78° C. The suspension is stirred for 30 min at 0° C. At −78° C. 1.34 mmol 3-oxopentylphosphonic acid diethylester (a)—in THF—are added dropwise thereto. The reaction mixture is stirred for 90 min at room temperature, then added to 40 ml ice cooled watery 10% ammoniumchloride solution and extracted three times with 30 ml methylenechloride respectively. The combined organic phases are dried over $MgSO_4$ and the solvent is removed under reduced pressure. The oxime 1 may be furthermore converted without further purification.

(Compare R. V. Hoffman, G. A. Buntain, Synthesis 1987, 9, 831–33 or an alternative preparation: T. Kawada, T. Tsushima, Heterocycles, 1989, 28, 573–578)

3-N-(Hydroxyamine)cyclopentylphosphonic acid diethylester 1(c)

Sodium cyanohydrideborate (NaBH₃CN) is used without further purification. To 4 mmol oxime 1(b) dissolved in little methanol 2 drops of bromocresol green is supplied and 6 n KOH is added dropwise thereto until a change of colour from yellow to green is observed. 3 mmol NaBH₃CN are added, stirred for 3 h at room temperature and quenched dropwise with methanol/HCl until a change of colour from green to yellow is observed. The reaction mixture is added to 10 ml of water and adjusted to pH>10 with 6 n KOH. After the watery phase is saturated with NaCl the solution is extracted 5 times with 10 ml chloroform respectively, dried over $MgSO_4$ and removed under reduced pressure. The yellow to red coloured raw product may be chromatographed on $SiO_2$.

(Compare R. F. Borch, M. D. Bernstein, H. D. Durst, J Am Chem Soc 1971, 93, 2897–904)

3-N-(Hydroxyamine)-cyclopentylphosphonic acid 1 (d)

130 ml concentrated HCl are added to 0.06 mol ester) 1(c) with cooling with ice and heated under vigorous stirring under reflux for 6 h. After cooling-off the yellow-brown coloured solution is concentrated under reduced pressure, taken up in approximately 30 ml of water and is treated with active carbon until a nearly colourless solution is produced. This is concentrated again under reduced pressure, taken up with approximately 30 ml of water and a pH of 4–5 is adjusted with NaHCO₃. The beige precipitate is filtered and can be washed with water/ethanol. 0.037 mol product is formed corresponding to a yield of 61%. Recrystallization is not necessary.

3-(N-formyl-N-hydroxyamino)-cyclopentylphosphonic acid mono sodium salt 1(e)

2 ml formic acid are added dropwise to 4 ml acetic anhydride at 0° C. within 5–10 min, are stirred for 10 min at the same temperature and for 15 min at room temperature, and the solution is cooled again to 0° C. 0.02 mol 3-N-(hydroxyamine) cyclopentylphosphonic acid (d) are dissolved in app. 6 ml formic acid during heating up to 40–50° C. and are added dropwise to the above solution at 0° C. and are stirred for 1 h at ambient temperature. Then it is concentrated to an oil under reduced pressure, taken up in water and concentrated under reduced pressure. This method is carried out for three times. In watery solution a pH of 4.5–5 is adjusted with 1 n NaOH. The resulting oil is extracted in isopropanol for several times whilst discarding the alcohol phase. The residue is taken up in methanol—until all is dissolved in the heat—and the product is precipitated by ethanol. After filtration of the raw product it may be recrystallised from methanol/ethanol once again.

EXAMPLE 2

3-Oxo-cyclohexylphosphonic acid diethylester 2(a)

0.52 mmol trimethylsilyltriflate is added dropwise to 11.4 mmol diethylphosphite and 12.4 mmol N,O-bis-(trimethylsilyl)acetamide in 5 ml dichlormethane at 0° C. After 30 minutes of stirring at the same temperature 0.52 mmol 2-cyclohexen-1-one are added dropwise thereto and is stirred for 1 h. The enolsilane intermediate product is hydrolized by 3 ml 1 n HCl during 3 hours of stirring. The organic phase is separated, dried over magnesiumsulfate and concentrated. The raw product can be chromatographed on $SiO_2$ and after concentration of the desired fractions results in 3-oxo-cyclohexylphosphonic acid diethylester 2(a) in a 95% yield.

(Compare I. Mori, Y. Kimura, T. Nakano, S. Matsunaga, G. Iwasaki, A. Ogawa, K. Hayakawa, Tetrahedron Letters 1997, 38, 3543–46)

3-(Phosphonic acid diethylester)cyclohexanone oxime 2(b) 2(b) may be synthesized by analogy to 1(b)

3-N-(hydroxyamine)-cyclohexylphosphonic acid diethylester 2(c)

Sodium cyanohydrideborate (NaBH$_3$CN) is used without further purification. To 4 mmol oxime 2(b) dissolved in little methanol 2 drops of bromocresole green are added and 6 n KOH is added dropwise thereto until a change of colour from yellow to green is observed. 3 mmol NaBH$_3$CN are added, stirred at room temperature for 3 h and quenched dropwise with methanol/HCl until a change of colour from green to yellow is observed. The reaction mixture is added to 10 ml water and a pH>10 is adjusted with 6 n KOH. After saturating the watery phase with NaCl the solution is extracted for 5 times with 10 ml chloroforme respectively, dried over MgSO$_4$ and removed under reduced pressure. The yellow to red coloured raw product may be chromatographed on SiO$_2$.

3-N-(hydroxylamine)-cyclohexylphosphonic acid 2(d)

2(d) is obtained in analogy to the hydrolysis of 1(c) with concentrated HCl in a yield of more than 50%.

3-(N-formyl-N-hydroxyamino) cyclohexylphosphonic acid monosodium salt 2(e)

Preparation of 2(e) see 1(e).

EXAMPLE 3

2,5-dichlorotetrahydrofurane 3(a)

At a temperature of –35° C. 142 g chlorine is condensed into 72 g absolute THF in 80 ml tetrachloromethane, which is diluted with nitrogen. Then it is exposed to a UV-lamp under stirring for 8–9 h. After the transformation has been completed CCl$_4$ is removed under reduced pressure. The products are firstly condensed into a condenser under high-vacuum which is cooled to –50° C., for being subsequently fractionated in water jet vacuum. 60 g 2,5-dichlorotetrahydrofurane having a boiling point$_{12\ Torr}$= 61–64° C. are achieved.
(Compare H. Gross, Chem. Ber 1962, 95, 83–90)

5-chlorotetrahydrofuryl-2-(phosphonic acid di-tert-butylester) 3(b)

31 g (160 mmol) di-tert-butylphosphite—dissolved in 90 ml THF is added dropwise to a suspension of 5.0 g 80% NaH (in mineral oil) in 60 ml absolute THF at 0° C. After 30 minutes of stirring at 0° C. 135 mmol 2,5-di-chlorotetrahydrofurane—dissolved in 120 ml absolute THF—is added dropwise at the same temperature. The reaction solution is boiled under reflux for 20 h and then concentrated under reduced pressure. An oil is achieved which is polluted by decomposition products of the educt 2,5-dichlorotetrahydrofurane, which can be separated by chromatography on SiO$_2$.
(Compare K. Baczko, W-Q. Liu, B. P. Roques, C. Garbay-Jauregiuiberry, Tetrahedron 1996, 52, 2021–30)

5-chlorotetrahydrofuryl-2-phosphonic acid 3(c)

0.9 mmol tert-butylester 3(b), 10 ml trifluoroacetic acid, 4.5 mmol anisole and 10 ml methylenechloride are stirred at room temperature for 1 h. Then 10 ml water are added dropwise thereto and it is concentrated until dryness. The resulting oil can be recrystallized from methanol and chloroforme.
(Compare T. R. Burke Jr., Z-H. Li, J. B. Bolen, V. E. Marquez, J Med Chem 1991, 34, 1577–81)

The hydrolysis of tert-butylester 3(b) may also be achieved by heating under reflux in benzene by adding trifluoroacetic acid (compare Chem. Ber. 1975, 108, 1732–44) or furthermore in pure trifluoroacetic acid at room temperature (compare Phosphorus, sulfur and silicium and related elements 1991, 61, 183–84).

Formohydroxamic acid 3(d)

is prepared according to a method of Bernhard et al. J. Am. Chem. Soc. 1964, 86, 4406 from hydroxyamine hydrochloride, potassiumchloride and potassiumhydroxyde, which all are used without further purification. Formohydroxamic acid: melting point: 74–77° C.

O-trimethylsilylformohydroxamic acid 3(e)

1 equivalent of formohydroxamic acid dissolved in THF is stirred under addition of triethylamine with 1 equivalent trimethylchlorsilane at room temperature for 2 days. O-trimethylsilylformohydroxamic acid is achieved in small yields and can be purified by column chromatography.

5-(N-formyl-N-hydroxyamino)-tetrahydrofuryl-2-phosphonic acid 3(f)

5-chlorotetrahydrofuryl-2-phosphonic acid is stirred with a 2-times-surplus of O-trimethylsilylformohydroxamic acid in absolute dimethylformamide at room temperature for 4 h. After quenching with water it is concentrated under reduced pressure, taken up in water, again concentrated, and the oil is chromatographed on cellulose.

EXAMPLE 4

2,6-dichlorotetrahydropyrane 4(a)

1 kg 25% watery solution of glutaraldehyde is extracted with methylenechloride, the organic phase is dried over Na$_2$SO$_4$, concentrated and glutaraldehyde is removed by distillation in vacuum (boiling point$_{13\ Torr}$=74–75° C.) Dry hydrochloric acid is introduced into a solution of 200 g glutaraldehyde dissolved in 700 ml absolute methylenechloride at –25° C. under vigorous stirring, whereby the temperature is kept under –15° C. It allowed to stand at –40° C. for 8 h, subsequently heated to 0° C. and separated from water. The organic phase is dried over Na$_2$SO$_4$, volatile constituents are removed under reduced pressure and finally 2,6-dichlortetrapyrane (a) is distilled (boiling point$_{0.01}$= 37–39° C.).
(Compare K. Dimroth, W. Kinzebach, M. Soyka, Chem. Ber. 1966, 99, 2351–60)

6-(N-formyl-N-hydroxyamino)-tetrahydropyryl-2-phosphonic acid 4(f)

Pyranderivative 4 can be produced from 2,6-dichlorotetrahydropyran as described under 3.

EXAMPLE 5

5-(oxo-pyrrolidine-2-yl)-phosphonic acid diethylester 5(a)

5-oxo-pyrrolidine derivative 5(a) can be obtained according to an instruction of J. Oleksyszyn, E. Gruszecka, P.

Kafafarski, P. Mastalerz, Monatsh. Chem. 1982, 113, 59–72 by the following synthesis sequence: Triethylphosphite and 3-chlorocarbonylpropionic acid methylester are converted to 4-(diethoxy-phosphoryl)-4-oxo-butyric acidmethylester. This is converted at the 4-oxo position to amine via the oxime. 4-amino-4-(diethoxyphosphoryl)butyric acid methylester is cyclized to the educt compound 5-(oxo-pyrrolidin-2-yl)-phosphonic acid diethylester 5(a) by heating for 30 minutes.

5-Thionopyrrolidine-2-phosphonic acid diethylester 5(b)

10 mmol of the oxo compound 5(a) are converted into the thio compound 5(b) by $P_4S_{10}$ in xylol under heating. After the reaction has been completed the yet hot xylol layer is decanted and the product is chromatographed on silica gelic acid.

5-Pyrrolidone oxime-2-phosphonic acid diethylester 5(c)

Hydroxyamine is set free from 4.5 g hydroxyamine hydrochloride suspended in 20 ml methanol by addition of 5.5 g $NaHCO_3$. 5 g 5-thionepyrrolidine 5(b) dissolved in methanol are added thereto. The solution is heated until the formation of $H_2S$ is completed (app. 12 h). Then methanol is distilled and the residue is further converted without further purification.
(Compare H. Behringer, H. Meier, Liebigs Ann. Chem 1957, 607, 67–91)

5-(N-hydroxyamino)-pyrrolidine-2-phosphonic acid diethylester 5(d)

The reduction of oxime 5(c) to hydroxyamine 5(d) is achieved according to the preparation of 1(c). The raw product shows a red colour, which can be removed by filtration upon active carbon with methanol as a solvent.

5-(N-hydroxyamino)-pyrrolidine-2-phosphonic acid 5(e)

Phosphonic acid diethylester 5(d) may be hydrolized in amounts up to 2 g of phosphodiesterase, which is coated on carboxymethylcellulose.
(Compare I. A. Natchev, Liebigs Ann Chem 1988, 861–867 and I. A. Natchev, Tetrahedron 1988, 44, 1511–22)

5-(N-formyl-N-hydroxyamino)-pyrrolidine-2-phosphonic acid 5(f)

The regiospecific formylation to N-formyl-N-hydroxylamine 5(e) at the nitrogen atom of hydroxyamine also results in a bis-formylation. As reagents for formylation 1,3,5-triformyl-hexahydro-1,3,5-triazine (produced from 1,3,5,7-tetraaza adamantane and formic acid; compare E. N. Gate, M. D. Threadgill, M. F. G. Stevens, D. Chubb, L. M. Vickers, J Med Chem 1986, 29, 1046–52), N-formylimidazole but also formic acid/acetic anhydride are used. 5(e) could not be isolated purely in substance by chromatography up to now.

EXAMPLE 6

Piperidin-2-on-6-Phosphonsäurediethylester [6](a)
6. When 5-amino-5-(diethoxyphosphoryl)pentanic acid is heated it cyclizes to 6(a).

Further steps also are in analogy to preparation of 5-(N-formyl-N-hydroxyamino)-pyrrolidine-2-phosphonic acid 5(e). Also 6-(N-formyl-N-hydroxyamino)-piperidine-2-phosphonic acid 6 has also not been obtained in substance up to now.

EXAMPLE 7a

Preparation of compounds HC(=O)—N(OH)—X—PO(OR)$_2$ with R=H or Na$^+$ and X=—CH$_2$—CH$_2$—C(=O)—

3-Chlorpropionyl-phosphonic acid-dimethylester

One equivalent of trimethylphosphite is added dropwise to 0.5 mol 3-chloropropionic acid chloride at 5° C., then heated to ambient temperature and stirred for further 2 h. The product is formed in good yields and may be distilled in an oil pump vacuum.
(by analogy to ref.: R. Karaman, A. Goldblum, E. Breuer, J. Chem Soc Perkin Trans I, 1989, 765–774; preparation of β-chloropropionic acid chloride compare: T. Bruylants, Bull. Soc. Chim. Belg. 1949, 58, 319)

3-(N-hydroxyamino)-propionylphosphonic acid dimethylester

Firstly 0.8 mol sodiumhydroxyd, dissolved in 75 ml water, then 75 ml methanol and subsequently 0.1 mol 3-chloro propionyl phosphonic acid dimethylester are added dropwise to a solution of 0.8 mol hydroxyaminohydrochloride in 100 ml water with cooling with ice. After 3 hours of stirring at a temperature of 40° C. methanol is removed under reduced pressure, the resulting watery solution is saturated with $NaHCO_3$, by-products are removed by washing with toluol and the product is shaken with methylenechloride, dried over magnesiumsulfate, filtered and removed under reduced pressure at room temperature. 3-(N-hydroxyamino)propionylphosphonic acid dimethylester remains.

3-(N-hydroxyamino)-propionylphosphonic acid 0.2 mol trimethylsilylbromide are slowly added to a solution of 0.1 mol 3-(N-hydroxyamino)-propionylphosphonic acid dimethylester in 100 ml of absolute acetonitrile. After 3 hours of stirring at room temperature the solution is concentrated and taken up in 50 ml methanol. After stirring for 30 minutes it is concentrated again. 3-(N-hydroxyamino)-propionylphosphonic acid may be further be converted without purification.
(by analogy to ref.: R. Karaman, A. Goldblum, E. Breuer, J. Chem. Soc. Perkin. Trans. 1,1989, 765–774)

3-(N-formyl-N-hydroxyamino)-propionylphosphonic acid mono sodium salt 2 ml formic acid are added dropwise to 4 ml acetic anhydride at 0° C., stirred for 10 min at the same temperature and 15 min at room temperature, again cooled to 0° C. and 0.02 mol 3-(N-hydroxyamino)propionylphosphonic acid, dissolved in formic acid are added dropwise at 0° C. After 1 hour of stirring at room temperature the solution is concentrated under reduced pressure, the oil is dissolved in 50 ml methanol, heated to 60° C. and a mixture of ethanol/isopropanol is added. Ein white solid precipitates, which may be dissolved in methanol once again and recrystallised from ethanol upon further addition of isopropanol.

Alternatively the following way of synthesis may be followed: The acid chloride of β-alanine is transformed with triethylphosphite into 3-aminopropionylphosphonic acid diethylester (compare B. A. Arbuzov, M. V. Zolotova, Bull.

Acad. Sci. USSR Div. Chem. Sci (Engl. Transl.) 1964, 1701–04). Subsequently it is formylated for oxidizing the resulting secondary amine to N-formyl-N-hydroxyaminophosphonic acid ester by dimethyldioxirane. The hydrolysis may be carried out as described above.

EXAMPLE 7b

Preparation of compounds HC(=O)—N(OH)—X—PO(OR)$_2$ with R=H or Na$^+$ and X=—CH$_2$—CH(OH)—C(=O)—

Instead of 3-chloropropionyichloride acrylic acid is proceeded from, transformed into the acid chloride, epoxidized by a peracid and the epoxide is opened radically to obtain 3-chloro-2-hydroxypropionylchloride. This may be transformed as in Example 7a.

EXAMPLE 7c

Preparation of compounds HC(=O)—N(OH)—X—PO(OR)$_2$ with R=H or Na$^+$ and X=—CH$_2$—CH$_2$—O—CH$_2$—

(2-chloroethoxy)methyl-phosphonic acid-diethylester 1-chloro-2-chloromethoxyethane (Preparation compare: B. Castro, Bull. Soc. Chim. Fr. 1967, 1533–40) is converted with triethylphosphite under reflux in a Michael Arbuzov reaction zum (2-Chlor-ethoxy)methylphosphonic acid diethylester.

(2-Azido-ethoxy)methyl-phosphonic acid-diethylester 0.02 mol (2-chloroethoxy)methyl-phosphonic acid diethylester, 3 mmol tetrabutylammoniumbromide and 2.5 g sodiumazide are boiled in 50 ml toluol under reflux for 4 h. After cooling-off it is washed for three times with 25 ml water respectively. The watery phase may be extracted with toluol. The combined toluol phases are dried over sodiumsulfate and the solvent is removed in the vacuum. A yellow oil remains.
(compare ref.: K. Eger, E. M. Klünder, M. Schmidt, J. Med. Chem. 1994, 37, 3057–61; also compare: A. Holy, I. Rosenberg, Collect. Czech. Chem. Commun. 1989, 2190–210)

(2-Aminoethoxy)methyl-phosphonic acid diethylester

The above obtained oil (24 mmol) dissolved in 5 ml toluol is added dropwise to a solution of 36 mmol triphenylphosphine in 35 ml toluol within 30 min. After one hour of stirring at room temperature 50 ml of water are added, vigously stirred for 15 min and the phases are separated. The watery phase is washed with ether for several times and concentrated. Traces of water are by the help of methanol. A yellow oil remains.
(compare Lit.: K. Eger, E. M. Klünder, M. Schmidt, J. Med. Chem. 1994, 37, 3057–61)

[2-(N-hydroxyamino)-ethoxy]methyl-phosphonic acid diethylester (2-aminoethoxy)methylphosphonic acid diethylester can be transformed to the corresponding hydroxyamine in little yields by the corresponding oxidationsmitteln known in literature (e.g. dimethyldioxirane or benzoylperoxide).

[2-(N-hydroxyamino)-ethoxy]methyl-phosphonic acid

With reference to K-L. Yu, J. J. Bronson, H. Yang, A. Patick, M. Alam, V. Brankovan, R. Datema, M. J. M. Hitchcock, J. C. Martin, J. Med. Chem. 1992, 35, 2958–2969 0.5 mol [2-(N-hydroxyamino)-ethoxy]methylphosphonic acid diethylester and 1 mol 2,4,6-collidine in 5 ml of absolute methylenechloride are stirred under argon for one hour at a temperature of 0° C. After allowing to stand for 16 hours at room temperature the solution is concentrated in vacuum, taken up in watery acetone and stirred for 14 hours. Subsequently it is taken up in in NaOH and heated to 100° C. for 2 h. After cooling-off it is concentrated and the raw product purified by chromatography.

[2-(N-Formyl-N-hydroxyamino)-ethoxy]methyl-phosphonic acid mono-sodium salt

Formylation may be carried out by analogy to the description of Example 7a.

EXAMPLE 7d

Preparation of compounds HC(=O)—N(OH)—X—PO(OR)$_2$ with R=H or Na$^+$ and X=—CH(OH)—CH(OH)—CH(OH)—C(=O)—

Starting point for X may be threonic acid, threose/erythrose or 2.3.4.4-tetrachlorobutyrylchloride (Cl$_2$C—CHCl—CHCl—COCl) known in literature.

What is claimed is:
1. Phosphorous organic compounds having a formula (I)

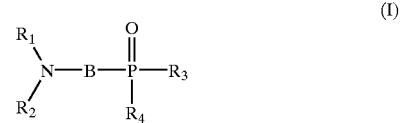

in which R$_1$ and R$_2$ are the same or different and are selected from the group consisting of hydrogen, substituted or unsubstituted alkyl, substituted and unsubstituted hydroxyalkyl, substituted and unsubstituted alkenyl, substituted and unsubstituted alkynyl, substituted and unsubstituted aryl, substituted and unsubstituted acyl, substituted and unsubstituted cycloalkyl, substituted and unsubstituted aralkyl, halogen, OX$_1$ and OX$_2$, wherein X$_1$ and X$_2$ may be the same or different and are selected from the group consisting of hydrogen, substituted or unsubstituted alkyl, substituted and unsubstituted hydroxyalkyl, substituted and unsubstituted alkenyl, substituted and unsubstituted alkynyl, substituted and unsubstituted aryl, substituted and unsubstituted acyl, substituted and unsubstituted cycloalkyl and substituted and unsubstituted aralkyl, and wherein B is an ether group represented by group (II)

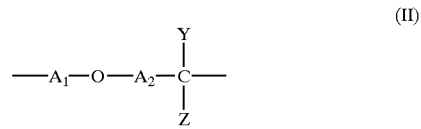

wherein A$_1$ and A$_2$, of which A$_2$ also may be absent, are the same or different and are selected from the group consisting of alkylene radicals, alkenylene radicals and hydroxyalkylene radicals, wherein Y and Z are hydrogen, R$_3$ and R$_4$ may be the same or different and are selected from the group consisting of hydrogen and halogens.

2. A composition comprising;

a first pharmaceutically active ingredient, the first pharmaceutically active ingredient being a compound according to claim 1; and a second pharmaceutically active ingredient.

3. The composition of claim 2 wherein the second pharmaceutically active ingredient is selected from the group consisting of sulfonamide, sulfadoxin, artemisinin, atovaquon, chinin, chloroquine, hydroxychloroquin, mefloquin, halofantrin, pyrimethamine, armesin, tetracycline, doxycyclin, proquanil, metronidazol, praziquantil, niclosamide, mebendazol, pyrantel, tiabendazole, diethylcarbazin, piperazin, pyrivinum, metrifonate, oxamniquin, bithionol and suramin.

4. The composition of claim 2 wherein the second pharmaceutically active ingredient is an antibiotic selected from the group consisting of penicillins, cephalosporins, β-lactam antibiotics other than penicillins and cephalosporins, tetracyclines, aminoglycosides, monobactams, β-lactamase inhibitors, chloramphenicols, quinolones, macrolides, glycopeptides, sulfonamides, lincosamides, streptogramins, clindamycin, fusidic acid, fosfomycin and folic acid.

5. A composition for treating infections comprising:

an effective amount of a compound according to claim 1; and a pharmaceutically acceptable excipient.

6. The composition of claim 5, wherein the infection is caused by bacteria.

7. The composition of claim 5, wherein the infection is caused by a virus.

8. The composition of claim 5, wherein the infection is caused by a parasite.

9. Phosphorous organic compounds having a formula (I)

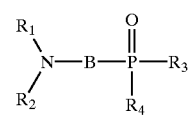

(I)

wherein $R_1$ and $R_2$ are independently selected from the group consisting of $OX_1$ and $OX_2$;

wherein $X_1$ and $X_2$ are independently selected from the group consisting of hydrogen, substituted or unsubstituted alkyls, substituted and unsubstituted hydroxyalkyls, substituted and unsubstituted alkenyls, substituted and unsubstituted alkynyls, substituted and unsubstituted aryls, substituted and unsubstituted acyls, substituted and unsubstituted cycloalkyls, substituted and unsubstituted aralkyls;

wherein $R_3$ and $R_4$ are independently selected from the group consisting of hydrogen and halogens;

wherein B is an ether group represented by group (II)

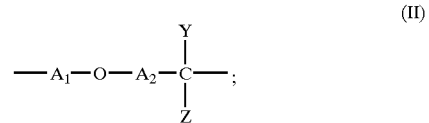

(II)

wherein $A_1$ is selected from the group consisting of alkylene radicals, alkenylene radicals and hydroxyalkylene radicals; and wherein $A_2$ may be absent or may be selected the group consisting of alkylene radicals, alkenylene radicals and hydroxyalkylene radicals.

* * * * *